United States Patent
Jeong et al.

(10) Patent No.: US 10,315,972 B2
(45) Date of Patent: Jun. 11, 2019

(54) SEPARATION METHOD AND SEPARATION PROCESS SYSTEM FOR RECOVERING ETHYLENE

(71) Applicant: LG CHEM, LTD., Seoul (KR)

(72) Inventors: Hoi In Jeong, Daejeon (KR); Jong Ku Lee, Daejeon (KR); Jeong Seok Lee, Daejeon (KR); Mi Kyung Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/321,224

(22) PCT Filed: Apr. 28, 2016

(86) PCT No.: PCT/KR2016/004461
§ 371 (c)(1),
(2) Date: Dec. 22, 2016

(87) PCT Pub. No.: WO2016/200052
PCT Pub. Date: Dec. 15, 2016

(65) Prior Publication Data
US 2018/0044266 A1    Feb. 15, 2018

(30) Foreign Application Priority Data

Jun. 9, 2015    (KR) .................... 10-2015-0081453

(51) Int. Cl.
| | |
|---|---|
| *C07C 11/04* | (2006.01) |
| *C07C 2/06* | (2006.01) |
| *C07C 7/04* | (2006.01) |
| *B01D 3/00* | (2006.01) |
| *C07C 7/00* | (2006.01) |
| *C07C 7/09* | (2006.01) |

(Continued)

(52) U.S. Cl.
CPC ............. *C07C 11/04* (2013.01); *B01D 3/002* (2013.01); *C07C 2/06* (2013.01); *C07C 7/005* (2013.01); *C07C 7/04* (2013.01); *C07C 7/09* (2013.01); *B01D 3/06* (2013.01); *B01D 3/322* (2013.01)

(58) Field of Classification Search
CPC .. C07C 11/04; C07C 2/06; C07C 2/04; C07C 7/04; C07C 7/00
See application file for complete search history.

(56) References Cited

U.S. PATENT DOCUMENTS

| | | | |
|---|---|---|---|
| 3,476,823 A | 11/1969 | Price et al. | |
| 3,607,963 A | 9/1971 | Danneil et al. | |

(Continued)

FOREIGN PATENT DOCUMENTS

| | | |
|---|---|---|
| CN | 102666443 A | 9/2012 |
| CN | 104245088 A | 12/2014 |

(Continued)

*Primary Examiner* — Youngsul Jeong
(74) *Attorney, Agent, or Firm* — Dentons US LLP

(57) ABSTRACT

The present invention relates to a separation method and a separation process system for easily recovering ethanol from an ethanol oligomerization reactant containing unreacted ethanol. A separation method according to the present invention may easily reflux ethylene while reducing or excluding the use of a reflux system which uses an expensive cooling medium, and the like, and thus may improve the economics while increasing separation efficiency.

14 Claims, 3 Drawing Sheets

(51) Int. Cl.
*B01D 3/06* (2006.01)
*B01D 3/32* (2006.01)

(56) References Cited

U.S. PATENT DOCUMENTS

| | | | |
|---|---|---|---|
| 7,476,775 B2 * | 1/2009 | Kreischer | ............... B01D 3/14 |
| | | | 202/152 |
| 7,718,838 B2 | 5/2010 | Woodard et al. | |
| 2012/0199467 A1 | 8/2012 | Gildenhuys et al. | |
| 2015/0133707 A1 | 5/2015 | Venter et al. | |
| 2017/0313634 A1 * | 11/2017 | Brown | ...................... C07C 2/32 |

FOREIGN PATENT DOCUMENTS

| | | | | |
|---|---|---|---|---|
| CN | 104284703 A | 1/2015 | | |
| EP | 1780189 B1 * | 5/2008 | ............... | C07C 2/22 |
| EP | 2738151 B1 | 6/2014 | | |
| JP | 61-69889 A | 4/1986 | | |
| KR | 10-0144700 B1 | 7/1998 | | |
| KR | 10-2015-0006067 A | 1/2015 | | |
| WO | 2013-168098 A1 | 11/2013 | | |
| WO | WO-2013168098 A1 * | 11/2013 | ............... | C07C 2/36 |

* cited by examiner

SEPARATION METHOD AND SEPARATION PROCESS SYSTEM FOR RECOVERING ETHYLENE

CROSS-REFERENCE TO RELATED APPLICATION

This application is a 35 USC § 371 National Stage entry of International Application No. PCT/KR2016/004461 filed on Apr. 28, 2016, and claims the benefit of Korean Patent Application No. 10-2015-0081453 filed on Jun. 9, 2015, all of which are incorporated by reference in their entirety for all purposes as if fully set forth herein.

TECHNICAL FIELD

The present invention relates to a separation method and a separation process system for easily recovering ethylene from an ethylene oligomerization reactant containing unreacted ethylene.

BACKGROUND ART

Linear alpha-olefin is an important substance used in comonomers, detergents, lubricants, plasticizers, and the like, and is widely used commercially. In particular, 1-hexene and 1-octene are widely used as comonomers for controlling the density of polyethylene when manufacturing linear low density polyethylene (LLDPE).

Linear alpha-olefins such as 1-hexene and 1-octene are typically prepared through an oligomerization reaction of ethylene. The ethylene oligomerization reaction is performed through an oligomerization reaction (trimerization or tetramerization) of ethylene using ethylene as a reactant, and the product produced through the reaction contains not only a multicomponent hydrocarbon mixture including the desired 1-hexene and 1-octene, but also unreacted ethylene. The product undergoes a separation process in a distillation column, during which unreacted ethylene is recovered and reused in the ethylene oligomerization reaction.

Hereinafter, typical process methods will be described with reference to FIGS. 1 and 2.

As illustrated in FIG. 1, a typical process for recovering unreacted ethylene is performed through a process system which includes a distillation column 200, a condenser 63, a reflux drum 80, and a reboiler 73. For example, ethylene oligomerization reactant is supplied to the distillation column 200 through a reactant supply line 10, and the relatively ethylene-rich top fraction is condensed by being transported to the condenser 63 through a top discharge line 60, and is then introduced into the reflux drum 80. Liquid phase components of the top fraction in the reflux drum 80 are reintroduced into the distillation column 200 through a first reflux line and gas phase components are discharged through a first recovery line 62. Moreover, a bottom fraction containing 1-hexene and 1-octene is introduced into the reboiler 73, and then vaporized and reintroduced into the distillation column through a second reflux line 71 or discharged through a second recovery line 72.

In addition, as illustrated in FIG. 2, a typical process for recovering unreacted ethylene is performed through a process system which includes a first flashing column 100, a distillation column 200, a condenser 63, a reflux drum 80, and a reboiler 73. For example, an ethylene oligomerization reactant is supplied to a first flashing column 100 through a supply line 10, a relatively ethylene-rich top fraction is recovered after being discharged through a first top discharge line 30, and a bottom fraction containing residual ethylene is supplied to the distillation column 200 through a first bottom discharge line 40. Next, the relatively ethylene-rich top fraction is condensed after being transported to the condenser 63 through a second top discharge line 60, and is then introduced into the reflux drum 80. The liquid phase components of the top fraction in the reflux drum 80 are reintroduced into the distillation column 200 through a first reflux line 61, and the gas phase components are discharged through a first recovery line 62. A bottom fraction containing 1-hexene and 1-octene is introduced into the reboiler 73 through a second bottom discharge line 70, and then vaporized and reintroduced into the distillation column 200 through a second reflux line 71 or discharged through a second recovery line 72.

Typical methods such as above necessarily use a large amount of a cooling medium during the process of condensing and refluxing ethylene due to the low boiling point of ethylene (about −103.7° C.), and the cooling medium is costly. Thus, there is a limitation of poor economic efficiency.

Therefore, there is a demand for an economically efficient method for recovering ethylene from an ethylene oligomerization reactant, in which unreacted ethylene may be easily separated and recovered.

PRIOR ART DOCUMENTS (Patent Document 1) KR2015-0006067 A
(Patent Document 2) U.S. Pat. No. 7,718,838 B2
(Patent Document 3) EP2738151 B1

DISCLOSURE OF THE INVENTION

Technical Problem

In order to resolve the above-described limitations, it is an objective of the present invention to provide a separation method for easily recovering ethylene from an ethylene oligomerization reactant.

Another objective of the present invention is to provide a separation process system for easily recovering ethylene from an ethylene oligomerization reactant.

Technical Solution

In order to address the above objectives, the present invention provides a separation method for recovering ethylene from an ethylene oligomerization reactant, the method comprising a first step for cooling the ethylene oligomerization reactant; a second step for flashing the cooled reactant to thereby separate the reactant into a first top fraction and a first bottom fraction; a third step for introducing the first bottom fraction into a distillation column, and recovering a second top fraction from the top of the column and a second bottom fraction from the bottom of the column; and a fourth step for condensing the recovered second top fraction, wherein the condensation is performed through a heat exchange between at least a portion of the first bottom fraction and the second top fraction.

In addition, the present invention provides a separation process system for recovering ethylene from an ethylene oligomerization reactant, the separation process system comprising a supply unit supplying the ethylene oligomerization reactant; a cooling unit connected to the supply unit and cooling the reactant; and a processing unit connected to the cooling unit and configured to separate ethylene from the cooled reactant, wherein the processing unit includes a flashing unit having at least one flashing column disposed therein, a recovery unit having a distillation column, a condenser, and a reboiler, and a circulation line which circulates the flashing unit and the recovery unit.

Advantageous Effects

A separation method for recovering ethylene from an ethylene oligomerization reactant according to the present invention may easily reflux ethylene while reducing or excluding the use of a condensation system which uses an expensive cooling medium, and the like, and thus may improve the economics while increasing separation efficiency.

BRIEF DESCRIPTION OF THE DRAWINGS

The following drawings are included in order to provide exemplary embodiments of the present invention and, together with the description, provide a better understanding of the technical features of the present invention. The scope of the present invention should not be construed as being limited to the features which are illustrated in the drawings.

MODE FOR CARRYING OUT THE INVENTION

Figure 1:
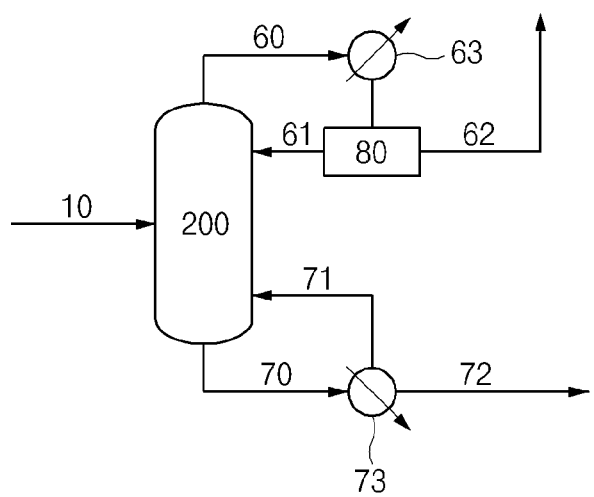
FIG. 1 schematically illustrates a typical process system for recovering ethylene from an ethylene oligomerization reactant.

Hereinafter, the present invention is described in greater detail to provide a better understanding of the present invention.

The terms used in the present disclosure and the claims should not be construed as being limited to their typical or dictionary definitions. Rather, the terms should be construed as being appropriately defined by the inventors in order to best describe the technical concepts of the present invention.

The present invention provides a separation method for recovering ethylene from an ethylene oligomerization reactant, wherein unreacted ethylene is easily recovered and economic cost is reduced.

Typically, linear alpha-olefins such as 1-hexene and 1-octene are important substances used in comonomers, detergents, lubricants, plasticizers, and the like, and are widely used commercially. In particular, linear alpha-olefins such as the above-described 1-hexene and 1-octene are typically prepared through an ethylene oligomerization reaction. The product obtained through the ethylene oligomerization reaction contains not only a multicomponent hydrocarbon mixture including the desired 1-hexene and 1-octene, but also contains a large amount of unreacted ethylene. In order to increase process efficiency, the unreacted ethylene is reused in the ethylene oligomerization reaction after being separated and recovered. The separation and recovery of unreacted ethylene may be performed through a distillation column, and in order to increase the recovery efficiency, a large amount of a cooling medium is used for reflux. However, the cooling medium is expensive and requires the installation of a separate cooling system, and thus methods using the cooling medium are limited in being economically inefficient. Therefore, a method which enables separation and recovery of ethylene at lower cost is needed in order to increase economic feasibility.

Thus, the present invention provides a separation method for recovering ethylene from an ethylene oligomerization reactant, wherein the economics and separation efficiency may be improved by easily condensing and refluxing ethylene while reducing or excluding the use of a reflux system that uses an expensive cooling medium.

The separation method according to an embodiment of the present invention includes a step for cooling an ethylene oligomerization reactant (step 1)); a step for flashing the cooled reactant to thereby separate the reactant into a first top fraction and a first bottom fraction (step 2)); a step for introducing the first bottom fraction into a distillation column, and recovering a second top fraction from the top of the column and a second bottom fraction from the bottom of the column (step 3)); and a step for condensing the recovered second top fraction (step 4)), wherein the condensation is performed through a heat exchange between at least a portion of the first bottom fraction and the second top fraction.

The step 1) is a step for cooling the ethylene oligomerization reactant having a relatively high temperature and pressure.

Prior to the cooling, the ethylene oligomerization reactant may have a temperature range of 50° C. to 100° C. and a pressure of at least 60 bar, and the cooling may be performed using cooling water such that the ethylene oligomerization reactant has a temperature of 30° C. to 50° C. and a pressure of 55 bar to 60 bar.

Meanwhile, the ethylene oligomerization reactant may be formed through an ethylene oligomerization reaction, and the ethylene oligomerization reaction may be an ethylene trimerization reaction or an ethylene tetramerization reaction. Moreover, the ethylene oligomerization reactant may be a multiphase multicomponent hydrocarbon containing ethylene oligomerization products, polymer products, and unreacted ethylene.

Specifically, the ethylene oligomerization reaction may indicate oligomerization of ethylene, and may be termed trimerization or tetramerization according to the number of oligomerized ethylenes, and collectively, may be termed multimerization. The ethylene oligomerization reaction according to an embodiment of the present invention may be used to selectively prepare 1-hexene and 1-octene, which are the main comonomers in linear low density polyethylene (LLDPE).

Such ethylene oligomerization reactions may be selective due to a catalyst system. The catalyst system may include a transition metal source that functions as a catalyst, a co-catalyst, and a ligand compound. The structure of an active catalyst may change according to the chemical structure of the ligand compound, and the selectivity of a generated substance may differ as a result.

The ligand compound may include at least two groups represented by Formula 1, and may include, as groups respectively connecting the at least two groups to each other with four carbon atoms, two or more groups, selected from among an aliphatic group having 1 to 20 carbon atoms, an alicyclic group having 3 to 20 carbon atoms, and an aromatic group having 6 to 20 carbon atoms, which are bonded together.

[Formula 1]

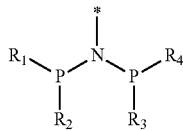

In Formula 1, $R_1$ to $R_4$ may be each independently an alkyl group having 1 to 20 carbon atoms, a alkenyl group having 2 to 20 carbon atoms, an aryl group having 6 to 20 carbon atoms, an arylalkyl group having 7 to 20 carbon atoms, an alkylaryl group having 7 to 20 carbon atoms, or an alkoxyaryl group having 7 to 20 carbon atoms.

Specifically, the ligand compound may include at least two diphosphinoamine functional groups connected by four carbon atoms, wherein groups connecting the diphosphinoamine functional groups may include two or more groups, selected from among an aliphatic group having 1 to 20 carbon atoms, an alicyclic group having 3 to 20 carbon atoms, and an aromatic group having 6 to 20 carbon atoms, which are bonded together.

The transition metal source functions as a catalyst and may be at least one selected from the group consisting of chromium(III)acetylacetonate, trichlorotris(tetrahydrofuran) chromium, chromium(III)-2-ethylhexanoate, and chromium (III)tris(2,2,6,6-tetramethyl-3,5-heptanedionate).

A group 13 metal-containing organometallic compound which is typically used when polymerizing ethylene in the presence of the catalyst may be used without particular limit as the co-catalyst. Specifically, the co-catalyst may be at least one compound among compounds represented by Formulas 2 to 4.

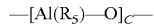 [Formula 2]

In Formula 2, $R_5$ is a halogen radical, a hydrocarbyl radical having 1 to 20 carbon atoms, or a halogen-substituted hydrocarbyl radical having 1 to 20 carbon atoms, and c is an integer of at least 2.

Specifically, a compound represented by Formula 2 may be a modified methylaluminoxane (MAO), a methylaluminoxane (MAO), an ethylaluminoxane, an isobutylaluminoxane, or a butylaluminoxane, and the like.

 [Formula 3]

In Formula 3, D is aluminum or boron, each $R_6$ is independently hydrogen, a halogen, a hydrocarbyl having 1 to 20 carbon atoms, or a halogen-substituted hydrocarbyl having 1 to 20 carbon atoms.

Specifically, a compound represented by Formula 3 may be trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tris-butylaluminum, tricyclopentylaluminum, tripentylaluminum, triisopentylaluminum, trihexylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, or tributylboron.

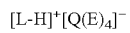 [Formula 4]

In Formula 4, L is a neutral Lewis base, $[L-H]^+$ is a Brønsted acid, Q is boron or aluminum having a oxidation state of +3, each E is independently an aryl group having 6 to 20 carbon atoms or an alkyl group having 1 to 20 carbon atoms, wherein at least one hydrogen atom is unsubstituted or substituted with a halogen, a hydrocarbyl having 1 to 20 atoms, an alkoxy functional group, or a phenoxy functional group.

Specifically, a compound represented by Formula 4 may be triethylammonium tetraphenylboron, tributylammonium tetraphenylboron, trimethylammonium tetraphenylboron, tripropylammonium tetraphenylboron, trimethylammonium tetra(p-tolyl)boron, tripropylammonium tetra(p-tolyl)boron, triethylammonium tetra(o,p-dimethylphenyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium tetraphenylboron, N,N-diethylanilinium tetraphenylboron, N,N-diethylanilinium tetrapentafluorophenylboron, diethylammonium tetrapentafluorophenylboron, triphenylphosphonium tetraphenylboron, trimethylphosphonium tetraphenylboron, triethylammonium tetraphenylaluminum, tributylammonium tetraphenylaluminum, trimethylammonium tetraphenylaluminum, tripropylammonium tetraphenylaluminum, trimethylammonium tetra(p-tolyl)aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetraphenylaluminum, N,N-diethylanilinium tetrapentafluorophenylaluminum, trimethylphosphonium tetraphenylaluminum, triphenylcarbonium tetraphenylboron, triphenylcarbonium tetraphenylaluminum, triphenylcarbonium tetra(p-trifluoromethylphenyl)boron, or triphenylcarbonium tetrapentafluorophenylboron.

In order to increase the selectivity and activity of the polymerization reaction, the mole ratio of ligand compound: transition metal source:co-catalyst in the catalyst system including the ligand compound, catalyst, and co-catalyst may be about 0.5:1:1 to about 10:1:10,000, and specifically about 0.5:1:100 to about 5:1:3,000.

Moreover, an active catalyst may be obtained by adding, simultaneously or in an arbitrary order, the ligand compound, the transition metal source, and the co-catalyst to a solvent in the presence or absence of a monomer. The solvent may include heptane, toluene, cyclohexane, methylcyclohexane, 1-hexene, diethylether, tetrahydrofuran, acetonitrile, dichloromethane, chloroform, chlorobenzene, methanol, or acetone, and the like.

The ethylene oligomerization reaction according to an embodiment of the present invention may be performed as a homogenous liquid phase reaction, a slurry reaction, a two-phase liquid/liquid reaction, a bulk phase reaction, or a gas phase reaction, and the like, by using the catalyst system and typical apparatus and contact techniques, in the presence or absence of an inert solvent.

The inert solvent may be, for example, benzene, toluene, xylene, cumene, heptane, cyclohexane, methylcyclohexane, methylcyclopentane, hexane, pentane, butane, or isobutene, and the like. Here, the solvent may be treated using a small amount of alkylaluminum to remove small amounts of water or air, and the like, which can act as a catalytic poison.

The ethylene oligomerization reaction may be performed in the presence of the catalyst system at a pressure of at least 60 bar and a temperature of 50° C. to 100° C.

The step 2) is a step for flashing the cooled reactant to thereby separate the reactant, which was cooled with the cooling water, into a first top fraction and a first bottom fraction. Here, the separated first top fraction may have a high ethylene content, and the first bottom fraction may have a low ethylene content. That is, the first top fraction may be an ethylene-rich fraction composed of mostly ethylene, and the first bottom fraction may be an ethylene-poor fraction containing, in addition to ethylene, a multiphase multicomponent hydrocarbon which contains ethylene oligomerization products and polymer products.

The at least a portion of the first bottom fraction may be used as a cooling medium for condensing a below-described second top fraction which is recovered from the top of the distillation column, and the flashing may be performed by being regulated such that the at least a portion of the first bottom fraction maintains a predetermined temperature difference with the second top fraction and is thus able to function as a cooling medium. Specifically, the flashing may be performed such that the temperature of the first bottom fraction is at least 3° C., specifically 5° C. to 50° C. lower than the temperature of the second top fraction. Moreover, the temperature difference between the at least a portion of the first bottom fraction and the second top fraction may be at least 3° C., specifically, 5° C. to 50° C. Here, the at least a portion of the first bottom fraction is equivalent to the first bottom fraction, and may be described as such merely in order to be indicated as being a portion of the first bottom fraction. That is, the at least a portion of the first bottom fraction may indicate the first bottom fraction itself, or indicate a portion separated from the first bottom fraction.

The flashing of the step 2) may be performed such that the temperature difference is present between the first bottom fraction and the second top fraction. The flashing condition is not particularly limited but may be performed as described below in greater detail.

The flashing of the step 2) may be performed as a one-step thermally insulated flashing under conditions which produce, from the cooled reactant, a first top fraction and a first bottom fraction having a pressure range of 5 bar to 20 bar. For example, the pressure of the first top fraction and the first bottom fraction may be equal to the process pressure in the distillation column after the flashing or, within the above pressure range, lower than the process pressure in the distillation column.

Moreover, the flashing of the step 2) may be performed as a two-step flashing in which a first high pressure flashing generating a third top fraction and a third bottom fraction is performed before the thermally insulated flashing which is performed under conditions producing the first top fraction and the first bottom fraction. Here, the third top fraction and the third bottom fraction may have a higher pressure than the first top fraction and the first bottom fraction respectively, and the third top fraction may be similar to the first top fraction in being an ethylene-rich fraction while the third bottom fraction may be similar to the first bottom fraction in being an ethylene-poor fraction.

The first top fraction and the third top fraction may be circulated and thereby reused in the ethylene oligomerization reaction.

The step 3) is a step for separating and recovering ethylene from the first bottom fraction by introducing the first bottom fraction into a distillation column and recovering a second top fraction from the top of the column and a second bottom fraction from the bottom of the column. Here, the second top fraction may be similar to the first top fraction in being an ethylene-rich fraction, and the second bottom fraction may be free of ethylene.

The distillation column may have a pressure of 5 bar to 20 bar, and the recovered second top fraction may have a temperature of −20° C. to 25° C.

The separation method according to an embodiment of the present invention may further include a step for filtering the first bottom fraction prior to performing the third step. Here, the filtering is not particularly limited and may be performed using a typical method known in the field. For example, the filtering may be performed using a filter or a decanter. Polymer products and other impurities may be removed from the first bottom fraction through the filtering.

The step 4) is a step for condensing the second top fraction in order to reintroduce at least a portion of the second top fraction recovered in the step 3) to the distillation column.

Figure 2:
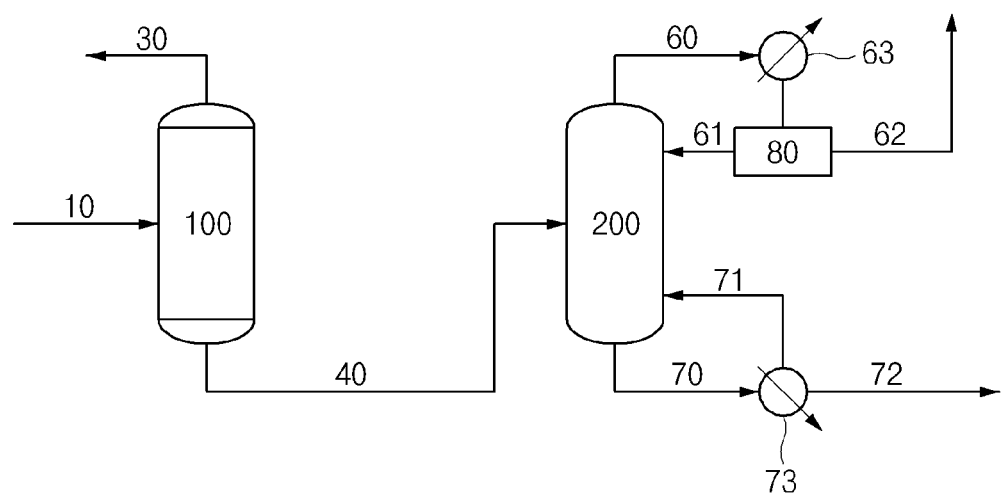
FIG. 2 schematically illustrates a typical process system for recovering ethylene from an ethylene oligomerization reactant, in which the process system includes a flashing column.

Typically, in order to achieve the above, a method was used in which the recovered second top fraction is reintroduced into the distillation column after being condensed using a condenser which uses a cooling medium and the like (see FIGS. 1 and 2). However, such condensation requires a large amount of an expensive cooling medium, and is thus limited in being uneconomical.

Conversely, a method using the step 4) according to an embodiment of the present invention may be used to perform a process for achieving the above objective without using a separate expensive cooling medium, and thus has a cost reducing effect.

Specifically, the condensation may be performed through a heat exchange between the at least a portion of the first bottom fraction and the second top fraction. That is, the condensation according to an embodiment of the present invention may be performed through the temperature difference between the at least a portion of the first bottom fraction and the second top fraction. The temperature difference between the at least a portion of the bottom fraction and the top fraction before the heat exchange may be at least 3° C., as described above. Here, the temperature of the at least a portion of the first bottom fraction may be −28° C. to 7° C. prior to the heat exchange.

After the heat exchange, the at least a portion of the first bottom fraction may be circulated and then introduced into the distillation column with the first bottom fraction of the step 3), and the at least a portion of the second top fraction may be condensed and reintroduced to the top of the distillation column while the remaining portion may be circulated and reused in the ethylene oligomerization reaction.

In addition the present invention provides a separation process system for recovering ethylene from an ethylene oligomerization reactant. The separation process system may be used to perform a separation process through the above separation method.

The separation process system according to an embodiment of the present invention includes a supply unit supplying an ethylene oligomerization reactant; a cooling unit connected to the supply unit and cooling the reactant; and a processing unit connected to the cooling unit and configured to separate ethylene from the cooled reactant, wherein the processing unit includes a flashing unit having at least one flashing column disposed therein, a recovery unit having a distillation column, a condenser, and a reboiler, and a circulation line which circulates the flashing unit and the recovery unit.

Hereinafter, the separation process system according to an embodiment of the present invention is described with reference to FIGS. 3 and 4. Here, descriptions other than those regarding the arrangement of equipment, design, and structure of the separation process system are identical to descriptions given with regard to the above-described separation method, and will thus be excluded.

The supply unit includes a supply line 10 which supplies an ethylene oligomerization reactant to the cooling unit, and the cooling unit includes a transport line 20 which transports the cooled reactant to the processing unit. Here, the cooling unit may be provided with a heat exchanger 11.

As described above, the processing unit may include a flashing unit having at least one flashing column; a recovery unit having a distillation column, a condenser, and a reboiler; and a circulation line which circulates the flashing unit and the recovery unit.

Figure 3:
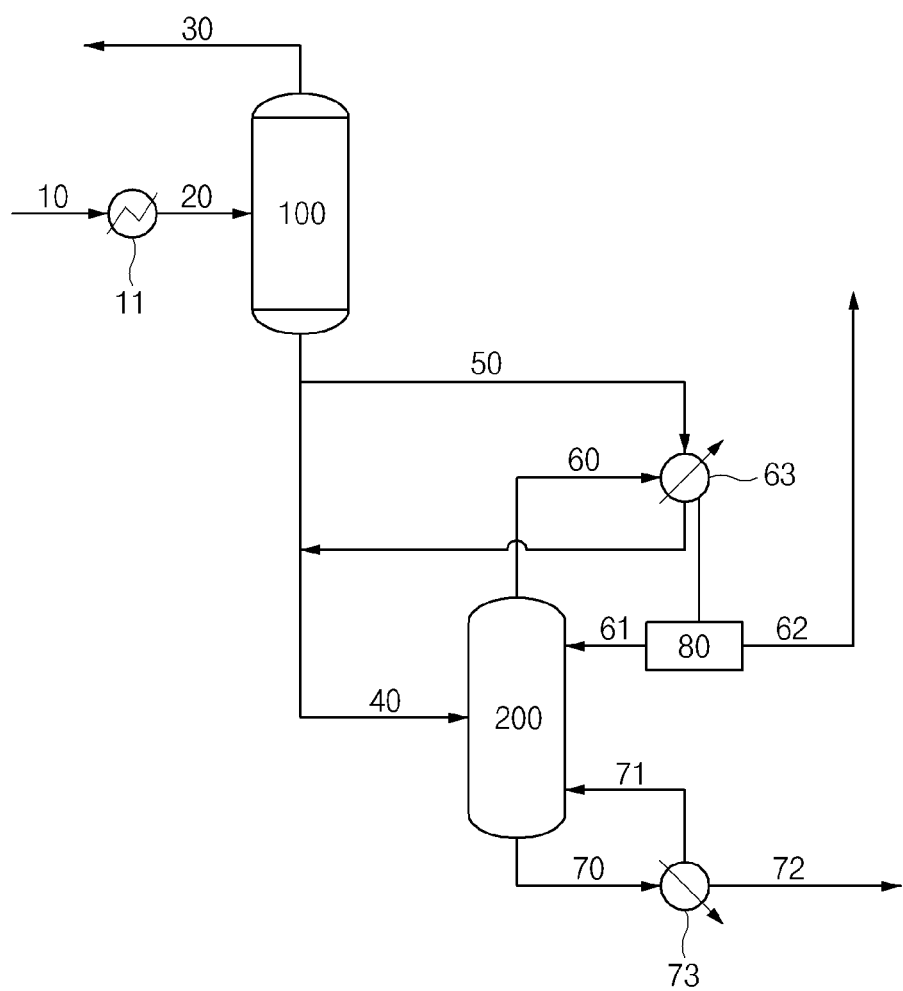
FIG. 3 schematically illustrates a process system for recovering ethylene from an ethylene oligomerization reactant according to an embodiment of the present invention, in which the process system includes a thermally insulated flashing column.
Figure 4:
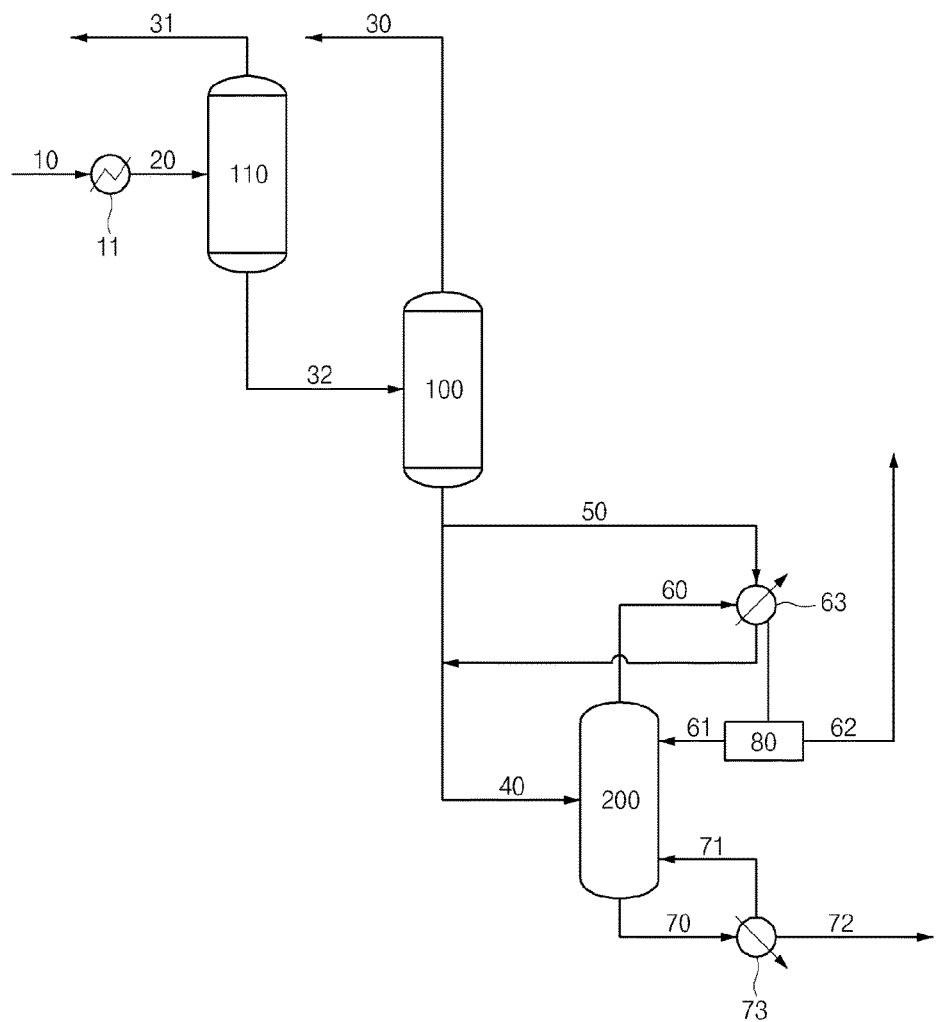
FIG. 4 schematically illustrates a process system for recovering ethylene from an ethylene oligomerization reactant according to an embodiment of the present invention, in which the process system includes a high pressure flashing column and a thermally insulated flashing column.

Specifically, the flashing unit according to an embodiment of the present invention may include a first flashing column 100 configured to perform thermally insulated flashing, and the first flashing column 100 may have a first top discharge line 30 which circulates a first top fraction and a first bottom discharge line 40 which transports a first bottom fraction to the recovery unit (see FIG. 3).

Moreover, the flashing unit according to an embodiment of the present invention may include a second flashing column 110 and a first flashing column 100 which are arranged in sequence, the second flashing column 110 performing high pressure flashing and the first flashing column 100 performing thermally insulated flashing. The second flashing column 110 may include a third top discharge line 31 which circulates a third top fraction and a third bottom discharge line 32 which transports a third bottom fraction to the first flashing column 100. The first flashing column 100 may include a first top discharge line 30 which circulates a first top fraction and a first bottom discharge line 40 which transports a first bottom fraction to the recovery unit (see FIG. 4).

The circulation line 50 may be connected from the first bottom discharge line 40 to the condenser 63 and circulate at least a portion of the first bottom fraction. That is, the at least a portion of the first bottom fraction may be transported through the circulation line 50 to the condenser 63 and used as a cooling medium for condensing a second top fraction, and may be recirculated through the first bottom discharge line 40 to the recovery unit.

The recovery unit is connected to the flashing unit, is configured to recover ethylene from the first bottom fraction which was transported through the first bottom discharge line 40, and includes a distillation column 200 connected to the first bottom discharge line 40, a condenser 63, a reboiler 73, and a reflux drum 80. The distillation column 200 includes a second top discharge line 60 for recovering a second top fraction and a second bottom discharge line 70 for recovering a second bottom fraction. The second top discharge line 60 may be connected from the top of the distillation column 200 to the condenser 63 and the bottom discharge line 70 may be connected from the bottom of the distillation column 200 to the reboiler 73. Moreover, the condenser 63 may be connected to a first reflux line 61 for reintroducing at least a portion of the second top fraction to the top of the distillation column 200, and the reboiler 73 may be connected to a second reflux line 71 for reintroducing at least a portion of the second bottom fraction to the bottom of the distillation column 200. Here, the first reflux line 61 may be connected, in sequence, to the condenser 63, the reflux drum 80, and the distillation column 200, and the second reflux line 71 may be connected, in sequence, to the reboiler 73 and the distillation column 200.

The second top fraction may be transported through the second discharge line 60 to the condenser 63, and the condenser 63 may condense the second top fraction by using, as a cooling medium, at least a portion of the first bottom fraction transported through the circulation line 50. Here, a separate condensation system using a cooling medium may be connected to the condenser 63, and the separate condensation system may be appropriately controlled to be used, as needed, when condensing the second top fraction.

The condensed second top fraction may be transported through the first reflux line 61 to the reflux drum 80. Gas and liquid phase components of the second top fraction may coexist inside of the reflux drum 80, and may be separated by the reflux drum 80 such that the liquid phase components of the second top fraction are reintroduced to the top of the distillation column 200 through the first reflux line 61, and the gas phase components of the second top fraction are discharged through a first recovery line 62 or circulated and reused in the ethylene oligomerization reaction.

Moreover, the second bottom fraction transported through the second bottom discharge line 70 to the reboiler 73 is vaporized and reintroduced to the bottom of the distillation column 200 through the second reflux line 71 or discharged through a second recovery line 72.

Hereinafter, the present invention is described in greater detail through examples. However, the following examples merely exemplify the present invention, and the scope of the present invention is not limited thereto.

In the following Example and Comparative Example, separation methods according to the present invention were simulated using the commercial process simulation program, ASPEN PLUS. Values such as those included in the program, disclosed in the literature, and obtained from previous ethylene separation and production processes were used as constants required by the simulation.

EXAMPLE

A process system was designed such as illustrated in FIG. 3. An ethylene oligomerization reactant containing 38.5 wt % of ethylene was cooled using cooling water after being transported through a supply line 10 to a heat exchanger 11. Next, the cooled reactant was flashed after being transported to a flashing column 100 through a transport line 20. Prior to being cooled, the ethylene oligomerization reactant was set at 60° C. and 60 bar, and the conditions for cooling were set so as to enable the ethylene oligomerization reactant to be at 40° C. and 60 bar after being cooled. The conditions for flashing were set so as to decrease the pressure to 10 bar and allow a first top fraction and a first bottom fraction having a temperature of −5° C. to be obtained. The process pressure of the distillation column was fixed at 10 bar and the distillation column was set so as to enable a second top fraction to be discharged at a temperature of 18° C. After being discharged at 18° C., the second top fraction was condensed to 8° C. through a heat exchange with the first bottom fraction. As a result of the heat exchange, the temperature of the first bottom fraction was increased to 0° C. Thus, it was verified that the first bottom fraction could completely replace a cooling medium.

COMPARATIVE EXAMPLE

Other than performing the simulation using a process system such as illustrated in FIG. 2, a process was performed using conditions identical to those in the Example. After flashing was performed under the same conditions as the Example, the temperature of a first top fraction and a first bottom fraction was 15° C., and a second top fraction could not be condensed to below 10° C. Thus, it is necessary to use an expensive cooling medium, and accordingly, additional cooling equipment is necessary.

The invention claimed is:

1. A separation method for recovering ethylene from an ethylene oligomerization reactant, the method comprising:
   1) cooling the ethylene oligomerization reactant to produce a cooled reactant;
   2) flashing the cooled reactant in a flashing column thereby separating the cooled reactant into a first top fraction comprising ethylene and a first bottom fraction;
   3) introducing at least a portion of the first bottom fraction into a condenser, and a remaining portion of the first bottom fraction into a distillation column, and recovering a second top fraction comprising ethylene from the top of the distillation column and a second bottom fraction from the bottom of the distillation column; and
   4) condensing the second top fraction in a condenser such that a temperature of the second top fraction is decreased,
      wherein the condensing is performed through a heat exchange using a temperature difference between the at least a portion of the first bottom fraction introduced into the condenser and the second top fraction, wherein a temperature of the at least a portion of the first bottom fraction prior to being introduced into the heat exchange is −28° C. to 7° C., and wherein the temperature difference between the at least a portion of the first bottom fraction and the second top fraction prior to being introduced into the heat exchange is 5° C. to 50° C.

2. The method of claim 1, wherein the ethylene oligomerization reactant of the step 1) has a temperature range of 50° C. to 100° C. and a pressure of at least 60 bar.

3. The method of claim 1, wherein the cooling is performed using cooling water such that the ethylene oligomerization reactant has a temperature range of 30° C. to 50° C. and a pressure of 55 to 60 bar.

4. The method of claim 1, wherein the flashing of the step 2) is performed such that a temperature of the first bottom fraction is 5° C. to 50° C. lower than a temperature of the second top fraction.

5. The method of claim 1, wherein the flashing of the step 2) is performed as thermally insulated flashing such that the first top fraction and the first bottom fraction produced from the cooled reactant have a pressure range of 5 to 20 bar.

6. The method of claim 1, wherein the first top fraction is circulated and reused in an ethylene oligomerization reaction.

7. The method of claim 1, wherein the flashing of the step 2) includes a high pressure flashing in order to produce a third top fraction and a third bottom fraction from the cooled reactant, which is followed by a thermally insulated flashing of the third bottom fraction in order to produce the first top fraction and the first bottom fraction which have a pressure range of 5 to 20 bar, wherein the third top fraction and the third bottom fraction having a higher pressure than the first top fraction and the first bottom fraction respectively.

8. The method of claim 7, wherein the third top fraction is circulated and reused in an ethylene oligomerization reaction.

9. The method of claim 1, wherein after the heat exchange, the at least a portion of the first bottom fraction is circulated and then introduced into the distillation column with the first bottom fraction of the step 3).

10. The method of claim 1, wherein after the heat exchange, obtaining a condensed second top fraction, and reintroducing at least a portion of the condensed second top fraction to the top of the distillation column.

11. The method of claim 1, wherein the second top fraction is circulated and reused in an ethylene oligomerization reaction.

12. The method of claim 1, wherein the ethylene oligomerization reactant is produced through an ethylene oligomerization reaction, the ethylene oligomerization reaction being an ethylene trimerization reaction or an ethylene tetramerization reaction.

13. The method of claim 1, wherein the ethylene oligomerization reactant is a multiphase multicomponent hydrocarbon containing ethylene oligomerization products, polymer products, and unreacted ethylene.

14. The method of claim 1, further comprising a step for filtering the first bottom fraction before the step 3).

* * * * *